United States Patent [19]

Edwards

[11] 4,083,227

[45] Apr. 11, 1978

[54] HYDROCARBON VAPOR ANALYZER

[75] Inventor: Ray C. Edwards, Kinnelon, N.J.

[73] Assignee: Edwards Engineering Corporation, Pompton Plains, N.J.

[21] Appl. No.: 784,029

[22] Filed: Apr. 4, 1977

[51] Int. Cl.² .............................................. G01N 31/06
[52] U.S. Cl. ........................................ 73/23; 23/254 R
[58] Field of Search ........................... 73/23; 23/254 R

[56] References Cited

U.S. PATENT DOCUMENTS

| 1,455,263 | 5/1923 | Oberfell | 73/23 |
| 2,147,607 | 2/1939 | McMillan et al. | 23/254 R |
| 2,601,272 | 6/1952 | Frost, Jr. | 73/23 |

Primary Examiner—Richard C. Queisser
Assistant Examiner—John P. Beauchamp
Attorney, Agent, or Firm—Daniel H. Bobis

[57] ABSTRACT

A hydrocarbon vapor analyzer for direct measurement of the percentage by volume of hydrocarbon vapor is a portable device utilizing two substantially identical vertically disposed graduated cylinders or burettes in which are mounted slidable and adjustable pistons for varying volumetric conditions and measuring changes in volumetric conditions of vapor mixtures of air and hydrocarbon being analyzed therein. One of the graduated cylinders defines a chamber for receiving the sample vapor mixture to be analyzed and the other provides a means for measuring the sample after it is transferred to the second burette through a device for absorbing the hydrocarbon vapor from the vapor mixture to be analyzed. The sample receiving burette has an operatively associated manifolding system which includes, an inlet valve for controlling the flow of the sample mixture of vapor to be analyzed to the sample receiving graduated cylinder, and a transfer valve for passing the vapor sample to be analyzed through the absorber for removing the hydrocarbon vapors to the graduated cylinder for measuring the net volume of hydrocarbon vapor absorbed from the sample mixture of vapor being analyzed. The respective pistons are individually slidable and adjustable by a suitable actuating device and can be set for simultaneous movement to permit controlled transfer of the sample mixture of vapor during operation of the instrument in accordance with prescribed analytical procedures for determining the percentage of hydrocarbon vapor present in the sample mixture being analyzed.

7 Claims, 6 Drawing Figures

HYDROCARBON VAPOR ANALYZER

BACKGROUND OF THE INVENTION

1. Field of the Invention

This invention relates to an improved hydrocarbon vapor analyzer that monitors the vapor content of mixtures of hydrocarbon vapors and air. More particularly the analyzer is suitable for use together with a hydrocarbon vapor recovery unit so as to determine the efficiency of the vapor recovery at an installation such as a gasoline bulk terminal, oil refinery, oil barge-loading and unloading operations, and at gasoline stations.

2. Description of the Prior Art

In the past hydrocarbon vapor analyzers were constructed largely for laboratory use. However these instruments, required the collection of the sample of the hydrocarbon vapor and air mixture to be analyzed at the site being monitored, transporting the sample to the laboratory, and then analysis of the collected sample.

Beyond the inconvenience of and possible variations in sample collection, the remoteness of the monitoring device to the site being monitored has been found by experience to dictate the extent to which such analyzing equipment can be employed.

In the more recent past, hydrocarbon vapor analyzers have been designed which were applicable to other than laboratory situations. However, these analyzers were so affected by ambient conditions that reliable results could not be obtained for example at a bulk gasoline terminal.

To overcome the shortcomings of the old designs and to provide an improved hydrocarbon analyzer which was relatively independent of sampling variations and ambient conditions, the rugged, economical analyzer of the present invention was developed.

SUMMARY OF THE INVENTION

Thus, the present invention covers a portable instrument designed for use under variable ambient conditions for measuring the percentage by volume or by way of hydrocarbon vapors present in a sample vapor mixture of air and hydrocarbon vapor which includes, a base, at least one pair of identical graduated cylinders or burettes disposed and connected substantially vertically on said base, one of said graduated cylinders operatively associated with manifolding means having an inlet for delivering to said graduated cylinder the sample vapor mixture to be analyzed, and a transfer valve, the other of said graduated cylinders connected through a hydrocarbon vapor absorber to the transfer valve so that the sample vapor mixture may be transferred to said other or second graduated cylinder when the transfer valve is open, said pair of graduated cylinders further provided with slidable and adjustable pistons or means to actuate the pistons independently and/or simultaneously to permit the sample vapor mixture to be analyzed to be drawn into the sample receiving graduated cylinders on opening of said inlet valve, and to be transferred to said measuring graduated cylinder when the inlet valve is closed and the transfer valve is open, and gauge means connected respectively to each of said graduated cylinders for determining the end point of the prescribed analytical procedures for determining the percentage of hydrocarbon vapor in the sample vapor mixture being analyzed.

Additionally valve means in the manifold means for purging the system, for verifying the accuracy of the operation of the system by known or standard vapor mixtures, and for determining whether the system has developed leakage therein.

By the prescribed analytical procedures for operating the portable instrument the date obtained can be utilized to determine directly the percentage of the hydrocarbon vapors present in the sample vapor mixture being analyzed, the extent of the hydrocarbon vapor recovered at various installations, such as bulk gasoline terminals, oil refineries, oil barge-loading and unloading facilities, and at gasoline stations.

An object of this invention is to provide an improved hydrocarbon vapor analyzer which is both simple to operate and suitable for use under field conditions.

Another object of this invention is to provide an instrument for monitoring the effectiveness of a hydrocarbon vapor recovery unit.

A yet further object of this invention is to provide an analyzer which is rugged in design, but is sufficiently portable so as to be readily moved from one location in a gasoline handling facility to another.

A feature of the present invention is a manifold arrangement for securely mounting the sample-receiving structure and efficiently arranging the control means.

Another feature of the present invention is to provide an improved mounting arrangement for the test apparatus.

Other objects and advantages of the invention will be apparent from the following detailed description taken in connection with the accompanying drawings wherein.

Figures 1, 2, 3, 4:
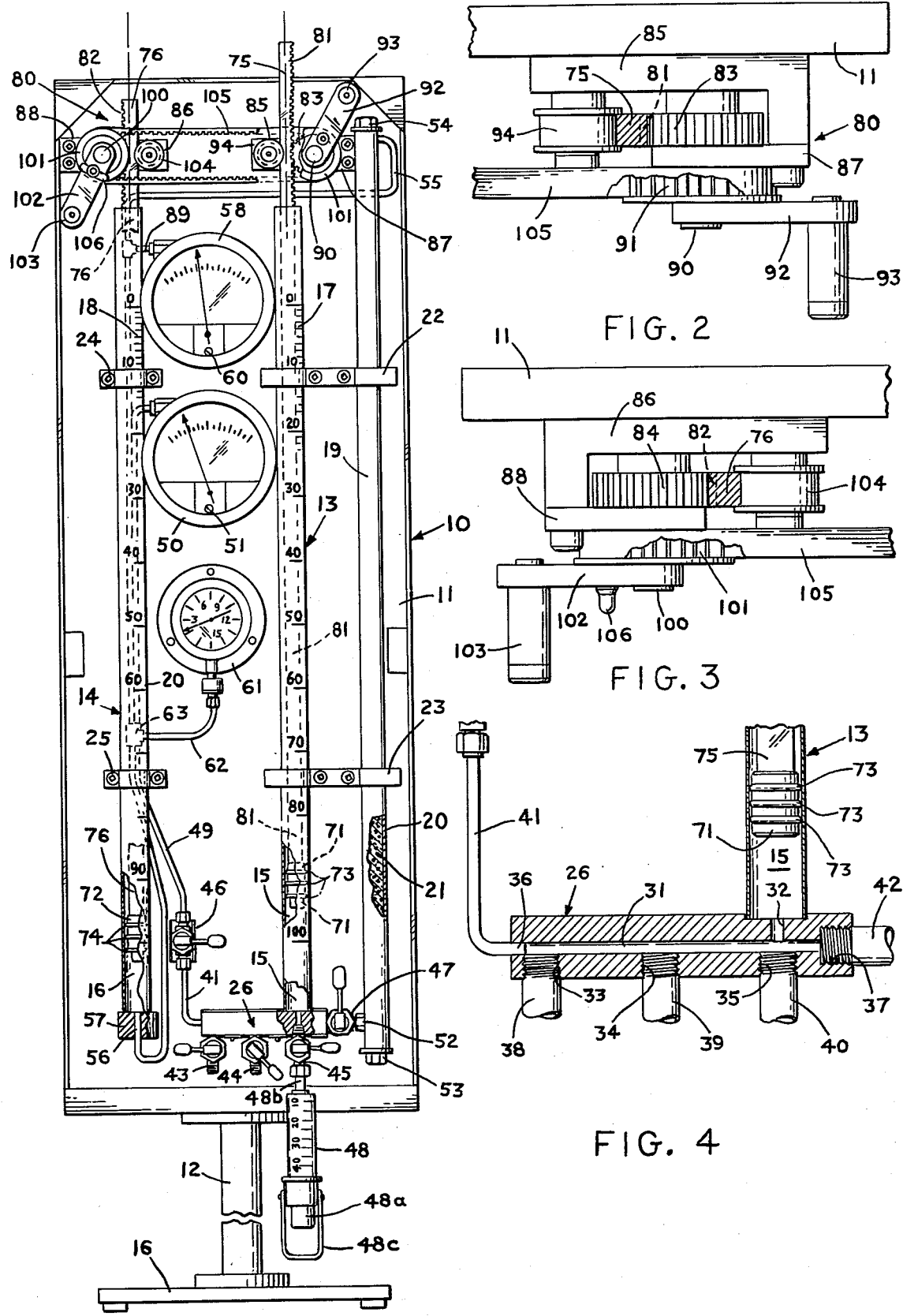
FIG. 1 is a front elevational view of an improved hydrocarbon vapor analyzer in accordance with the present invention.
FIG. 2 is a partial top elevational view of the hydrocarbon vapor analyzer of FIG. 1 showing the actuating means for the piston in the sample-receiving graduated cylinder or burette.
FIG. 3 is a partial top elevational view of the hydrocarbon vapor analyzer of FIG. 1 showing the actuating means for the piston in the measuring graduated cylinder or burette.
FIG. 4 is a cross-sectional view of a valve block and piston of the hydrocarbon vapor analyzer of FIG. 1.

Referring to the drawings FIG. 1 shows one portable type hydrocarbon vapor analyzer instrument in accordance with the present invention generally designated 10. The analyzer 10 has an instrument panel 11 which is detachably connected to a suitable base generally designated 12 which permits the analyzer to be transported and placed in juxta position to any given hydrocarbon vapor recovery system, device, or other chemical system on which it is desired to monitor and sample the hydrocarbon vapor present in mixtures of air and hydrocarbon delivered to said recovery systems, devices or other systems and/or the hydrocarbon present in the air and hydrocarbon vapor affluents from said systems.

FIG. 1 shows that analyzer 10 includes a pair of conventional graduated cylinders or burettes 13 and 14 which define fluid or vapor chambers 15 and 16 respectively therein having generally a 100 cc capacity. The graduations as at 17 and 18 on the respective graduated cylinders being marked in 10 cc intervals from the zero cc marking at the top to the 100 cc marking at the bottom of the graduated cylinders.

The graduated cylinder or burette 13 receives the sample vapor mixture of air and hydrocarbon vapor to be analyzed in the sample chamber 15 formed therein. This vapor mixture sample is delivered through an absorber 19 to the other graduated cylinder or burette 14 as is more fully described below. In the absorber 19 a chamber 20 holds an activated charcoal mixture which acts to absorb the hydrocarbon vapor from the vapor mixture sample as it is passed from graduated cylinder 13 to the graduated cylinder 14 and in graduated cylinder 14 the remaining portion of the mixture is measured to determine how much of the hydrocarbon vapor in the original vapor mixture sample has been absorbed and thus provide a direct measurement as to the percentage of hydrocarbon vapor present in the vapor mixture sample originally delivered to the graduated cylinder or burette 13.

It is believed that those skilled in the art will understand that in the case of a hydrocarbon vapor recovery system that if samples of the inlet vapor mixture and samples of the outlet vapor mixture are correlated that the net hydrocarbon vapor recovery for the particular hydrocarbon vapor recovery system can be determined as will be more fully described and explained below.

FIG. 1 further shows that graduated cylinder 13 and the hydrocarbon vapor absorber 19 are mounted adjacent to each other so they can be connected on the instrument panel 11 by spaced dual clamps as at 22 and 23. Similarly at a spaced distance from the graduated cylinder 13 the graduated cylinder or burette 14 will also be connected to the instrument panel 11 by means of spaced single clamps 24 and 25.

The lower end of the graduated cylinder or burette 13 is fixedly connected in fluid tight engagement with a valve manifold 26.

The valve monitored 26 is necessary and desirable because in addition to providing means for passing vapor mixture samples to be analyzed to the graduated cylinder 13, there are several other procedures required for the proper functioning of this instrument, such for example as verifying the accuracy of the system by utilizing a known or standard sample, and testing of the system for leaks.

Valve manifold assembly 26 not only has valving means to facilitate introduction of the vapor mixture samples into the graduated cylinder 13, and for transferring of this vapor mixture sample through the absorber 19 to the graduated cylinder or burette 14 but additionally has valving means to permit the other procedures desirable and necessary to the proper operation of this instrument as will now be described.

Accordingly referring to FIG. 1 and 4 the valve manifold assembly 26 is shown to include an elongated body or block 30 which has a centrally disposed passage 31 extending in the longitudinal axis thereof.

A connecting bore 32 connects the central passage 31 with the vapor chamber 15 formed in the graduated cylinder 13 so that vapor mixtures can be passed from the central passage 31 into and out of the vapor chamber 15 and graduated cylinder 31.

Elongated body or lock 30 is provided with a plurality of inlet ports as at 33, 34 and 35 in the side wall and with outlet or transfer ports as at 36 and 37 at the respective ends thereof. Which ports respectively connect freely with the central passage 31 and with each other as will be clear by reference to FIG. 4 of the drawing.

Each of the ports 33, 34, 35, 36, and 37 are connected by suitable connecting lines as at 38, 39, 40, 41 and 42 to operatively associated inlet valves 43, 44 and 45 and transfer valves 46 and 47. The inlet valves 43 and 44 provide alternate means for introducing a vapor mixture sample into the graduated cylinder 13 or when opened to balance the system at atmospheric pressure. Inlet valve 44 provides a means for connecting a syringe 48 for establishing a known or standard air-hydrocarbon vapor mixture for verifying the accuracy of the operation of the instrument as is more fully described below.

Transfer valve 46 connects at the side opposite from the port 36 and line 41 to connecting gauge line 49 which connects to the inlet of the pressure gauge 50 which functions to show the pressure present in the vapor chamber 15 of the graduated cylinder 13. The pressure gauge 50 will be any type of conventional pressure gauge for instruments of which there are many easily purchaseable on the open market and will contain a zero adjusting screw as at 51.

The transfer valve 47 is connected at the end opposite from the valve manifold 26 to an inlet port 52 in the hydrocarbon vapor absorber 19. Thus when the transfer valve 47 is open it can pass any vapor mixture sample from the graduated cylinder 13 to the inlet end of the chamber 20 in the absorber 19.

Absorber 19 is an elongated cylindrical device which forms the chamber 20 in which activated charcoal 21 is stored. Closure members as at 53 and 54 are threadibly connected at opposite ends of the absorber 19 and can be easily removed to permit used activated charcoal to be emptied from the chamber 20 and replaced with fresh activated charcoal as may be necessary for proper operation of the hydrocarbon vapor analyzer 10. Depending on the clarity of the activated charcoal used in the absorber 19, a single charge of charcoal can be expected to absorb more than 500 cc of hydrocarbon vapor before it must be removed and replaced with fresh activated charcoal. Thus, a given charge of activated charcoal in the absorber 19 can be utilized for many tests.

Connected to the end of the absorber 19 remote from port 52 is a transfer or connecting line 55 which connects the absorber 19 to a port 56 formed in a mounting block 57 to which the graduated cylinder 14 is connected in fluid tight engagement all of which is shown in FIG. 1 of the drawings.

The port 56 communicates with the vapor chamber 16 formed by the graduated cylinder 14 and therefore permits that portion of the vapor mixture sample that is not absorbed in the hydrocarbon vapor absorber 19 to be passed and delivered into the vapor chamber 16 of the graduated cylinder 14 so as to leave a measured quantity of the graduated cylinder 14 that is not filled by this mixture as representative of the percentage of hydrocarbon vapor that was present in the original vapor mixture sample passed to the graduated cylinder 13 as will be clear from the description of the procedures for analyzing a vapor mixture sample as is set forth more fully below.

A pressure gauge 58 is connected by a guage line 59 to the transfer or connecting line 55 and acts to register the pressure in the vapor chamber 16 of the graduated cylinder 14. The pressure gauge 58 may be any conventional type of instrument gauge many of which are purchaseable on the open market and similar to gauge 50 will have a xero setting screw 60 all of which is shown in FIG. 1 of the drawings.

A system pressure gauge 61 is connected by line 62 to a T-fixture 63 disposed across the respective transfer or connecting line 55 and the gauge line 49 so that it can be brought into communication with all portions of the various elements and connecting lines of the system when the valves 46 and 47 are moved to open position. The system pressure gauge 61 is also a conventional pressure gauge for instruments which is easily purchaseable on the open market.

In order to control the quantity of the vapor mixture sample introduced into the graduated cylinder 13 and to pass and transfer the same through the absorber 19 to the graduated cylinder 14, a pumping assembly generally designated 70 is provided as is shown in FIGS. 1, 2 and 3 of the drawings.

The pumping assembly 17 includes a first piston 71 reciprocatably and slidably mounted in the vapor chamber 15 of the graduated cylinder 13 and a second piston 72 reciprocatably and slidably mounted in the vapor chamber 16 of graduated cylinder 14.

The piston 71 is maintained in fluid tight engagement with the walls of the vapor chamber 15 by means of O-rings 73 and the piston 72 is maintained in fluid tight engagement with the vapor chamber 16 of graduated cylinder 14 by means of O-rings 74.

In order to reciprocate the respective pistons 71 and 72 in the vapor chambers 15 and 16, an elongated connecting rod 75 is connected to the top of piston 71 and an elongated connecting rod 76 is connected to the top of piston 72. Connecting rods 75 and 76 are sized to fit in the longitudinal axis of the vapor chambers 15 and 16 respectively and have a length not only sufficient to move the respective pistons 71 and 72 through the full volumetric capacity of the vapor chambers 15 and 16 in the graduated cylinders 13 and 14 but further to permit the connecting rods 75 and 76 to extend out of the respective open ends of the graduated cylinder 13 and 14 for engagement respectively with actuating means generally designated 80 as is shown in FIGS. 1, 2 and 3 of the drawings.

In the illustrated form of the present invention, the actuating means 80 is connected respectively to the elongated connecting rods 75 and 76 to permit both independent reciprocation of the piston 71 and 72 or simultaneous movement thereof as may be required by the procedures for analyzing a given vapor mixture sample as is more fully described below.

Thus referring to FIGS. 1, 2 and 3 the elongated connecting rods 75 and 76 are shown as provided with gear teeth to form linear extending racks 81 and 82 which lie in the longitudinal axis of the respective graduated cylinders 13 and 14 and through the actuating means 80 for operative association with pinion gears as at 83 and 84 rotatably mounted in the respective right pinion bracket 85 and left pinion bracket 86.

Right pinion bracket 85 and left pinion bracket 86 are connected in spaced relation to the instrument panel 11 and are provided respectively with a right bracket plate 87 and left bracket plate 88.

A right driving shaft 90 is rotatably mounted in the right bracket plate 87 and right pinion bracket 85 so that the pinion gear 83 can be fixedly connected thereto inboard of the right bracket plate 87 and a pulley 91 connected outboard of the right bracket plate 87 as is shown at FIG. 2 of the drawings. This will permit a crank 92 having a handle 93 to be connected to the outboard end of shaft 90 to provide means for rotating the pinion gear 83 and pulleys 91 simultaneously when the crank 92 is turned.

An idler or guide roller 94 is provided on the side of the elongated connecting rod 75 remote from the pinion gear 83 to insure that when the connecting rod 75 is moved by rotation of the pinion gear 83 that the connecting rod 75 will move in the longitudinal axis of the graduated burette 13.

In a similar fashion a left driving shaft 100 is rotatably mounted in the left bracket plate 88 and left pinion bracket 86 so that the pinion gear 84 can be fixedly connected for rotation by the shaft 100 inboard of the left bracket plate 88 and a left pulley 101 can be fixedly connected for rotation by the driving shaft 100 outboard of the left bracket plate 88 as is shown in FIG. 3 of the drawings and a crank 102 with a handle 103 will be connected to the outboard end of drive shaft 100 so that when the crank 102 is rotated it will act to drive both the pinion gear 84 and the pulley 101.

In idler guide 104 it is also rotatably mounted on the left pinion bracket 86 on the side of the elongated connecting rod 76 remote from the pinion gear 84 so that when the pinion gear 84 is rotated to move the connecting rod 76 the connecting rod 76 will move in the longitudinal axis of the graduated cylinder 14.

FIGS. 1, 2 and 3 show that the pulleys 91 and 101 are connected by a pulley belt 105. However, because the pulley 101 is freely rotatable on the drive shaft 100 rotation of the crank 92 or crank 102 will not act to drive the respective opposite pinion gears.

However when it is desired to move the respective connecting rods 75 and 76 simultaneously a suitable clutch means can be operated by the wing nut 106 provided on the crank 102 as is shown in FIGS. 1 and 3 of the drawings. If the wing nut 106 is engaged then whether the crank 92 or 102 is rotated, it will depending on the direction of rotation cause one connecting rod and the piston connected thereto to rise in one of the graduated cylinders and the other connecting rod and the piston connected thereto to fall in the other graduated cylinder and of course as will be obvious to those skilled in the art, the reverse will be true when the direction of rotation of the pulley 105 is changed.

OPERATION OF HYDROCARBON VAPOR ANALYZER

To measure the precent by volume of hydrocarbon vapor in a vapor mixture of air and hydrocarbon vapor, the apparatus as described above will be utilized in accordance with the following procedure.

The syringe 48 which is utilized to verify the accuracy of the analyzer 10 as is herein after described will be moved from the apparatus when it is being operated to measure percent by volume of hydrocarbon vapor.

Further either valve 43 or 44 can be used where a single vapor mixture sample is being analyzed. However these two valves are necessary where the hydrocarbon vapor analyzer is being used to evaluate the performance or the effective recovery that is accomplished by a hydrocarbon vapor recovery system. Such performance of a hydrocarbon vapor recovery system can be determined by using these inlet valves so that the percent of hydrocarbon vapor by volume in the vapor mixture entering the hydrocarbon vapor recovery unit can be compared to the percent of hydrocarbon vapor by volume in the vapor mixture discharge from the hydrocarbon vapor recovery unit.

Figure 5:
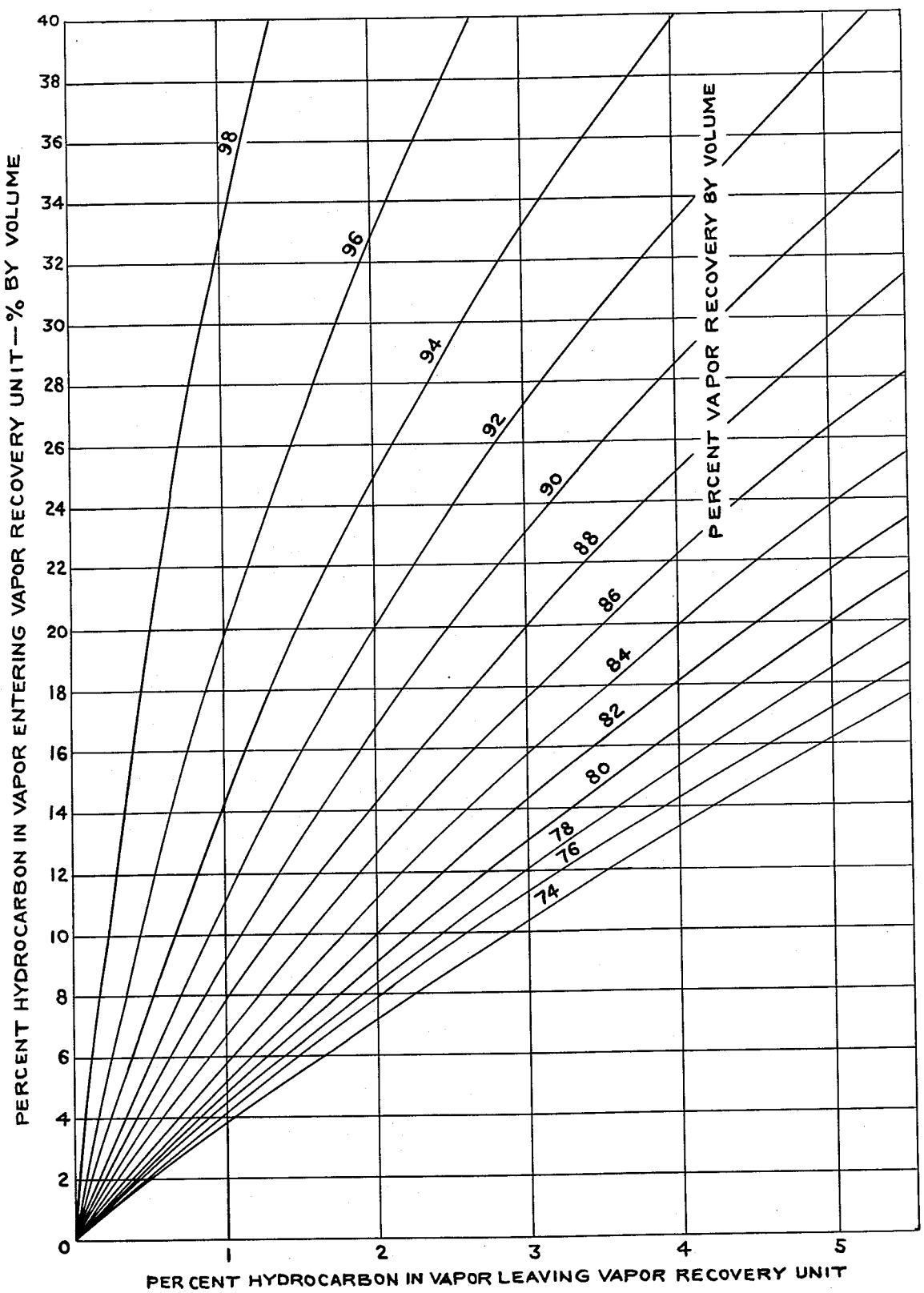
FIG. 5 is a graph by which the volumetric efficiency of a hydrocarbon vapor recovery apparatus is determined utilizing data from application of the present invention.

By means of the illustrated graph at FIG. 5 these two values can be compared quickly once the given inlet sample and outlet sample have been analyzed to provide their respective percent by volume of hydrocarbon vapor in the given samples.

For this purpose the inlet or entering vapor mixture to the hydrocarbon vapor recovery unit will be connected to valve 43 and the outlet or discharge vapor mixture leaving the hydrocarbon vapor recovery unit will be connected to valve 44 and of course with this arrangement continuous sampling can be done while the hydrocarbon vapor recovery unit is in operation.

The sampling of course must be done alternatively because each sample must be separately tested in the manner now to be described.

Thus, either sample valve 43 or 44 may be connected by suitable tubing to the source of vapor to be analyzed or alternatively "grab" samples may be brought to either valve 43 or 44 to be analyzed.

With the syringe removed from the instrument, valves 43, 44, 45, 46 and 47 are first all closed and then valve 45 is opened.

The wing nut 106 is opened so that the pulley belt 105 will not be driving the shafts 90 and 100 simultaneously.

By means of crank 92 the piston 71 is run up and down in graduated cylinder 13 for the purpose of purging the cylinder and then the piston 71 is placed in the lower most position at which a reading of 100 cc is indicated.

Next valve 47 is opened and gauge 58 should give a zero reading after a few minutes. If gauge 58 does not give a zero reading then the zero adjustment screw 60 is adjusted to set the gauge 58 at zero.

When a zero set reading is achieved for the gauge 58, valve 47 is closed.

Valve 45 is now closed when valve 43 (or 44) is opened and a 100 cc sample of the vapor mixture to be analyzed is drawn into the graduated cylinder or burette 13 by rotating the crank 92 to move the piston 71 upwardly to the zero position.

Valve 43 is then closed and valve 45 opened and by reversing the direction of rotation of crank 92, the piston is moved downwardly in the graduated cylinder 13 to expel the 100 cc sample in the vapor chamber 15 of the graduated cylinder 13. The purpose of this operational step is to purge the manifolding and graduate cylinder 13 of all non-sample vapors.

Valve 45 is now again closed and valve 43 opened and once again by means of the crank 92 a second 100 cc sample of the vapor mixture to be analyzed is drawn into the graduated cylinder or burette 13.

Valve 43 is now closed and valve 45 again opened to permit the vapor mizture sample in vapor chamber 15 of the graduated cylinder or sample burette 13 to come to atmospheric pressure. This will occur automatically after a few minutes and then valve 47 is opened until the pressure gauge 58 balances out to a zero pressure reading at which time valve 45 is again closed.

Since valve 47 is still open the crank 92 can be turned in a direction to lower the piston 71 until the pressure gauge 58 reads 0.5 inch.

At this point the system is ready to determine the percent volume of hydrocarbon present in the vapor mixture sample of air and hydrocarbon in the graduated cylinder 13 and this is done in the following manner.

The wing nut 106 is tightened so that when crank 92 is turned it will cause both the connecting rod 75 and connecting rod 76 to move the respective associated pistons 71 and 72 connected thereto in different directions dependent on the direction that the crank 92 is rotated as has been described.

In the present procedure crank 92 is rotated to lower the piston 71 and this will simultaneously cause the piston 72 to raise as the vapor mixture sample transfers from the fluid chamber 15 through valve 47, absorber 19, connecting or transfer line 55 and port 56 into the fluid chamber 16 of the graduated cylinder 14.

The piston 71 is lowered carefully and the pressure readings on gauge 58 are observed as this is done. If the pressure readings on gauge 58 drop below zero, the wing nut 106 is released or loosened so that the pulley 101 will free wheel once again and the pressure on gauge 58 is again reset to 0.5. The wing nut 106 can then be retightened and the crank 92 again rotated to continue lowering the piston 71 and the sampling steps for maintaining the pressure on pressure gauge 58 within the above parameters repeated until the piston 71 indicates a reading of 100 cc to show that the vapor mixture sample in the fluid chamber 15 has been discharged from the graduated cylinder 13.

Wing nut 106 is now loosened any by means of the crank 102 the piston 72 is moved so as to adjust the pressure setting of gauge 58 to zero.

The number of cc's on the graduated cylinder or measuring burette 14 above the top of the piston 72 is then read and this reading represents the percent of hydrocarbon by volume that was present in the vapor mixture sample orginally delivered to the graduated cylinder 13 as above described.

After the reading has been recorded valve 45 is then opened and crank 102 operated to lower the piston 72 to the bottom of the fluid chamber 16 in the graduated cylinder or measuring burette 14.

After a short additional waiting period the pressure in pressure gauge 58 should drop to zero and when this occurs the analysis is terminated and the instrument is ready to receive another vapor mixture sample for analysis.

Where the hydrocarbon vapor analyzer in accordance with the present invention as above described is utilized in conjunction with a hydrocarbon vapor recovery system, then by alternate use of samples from the inlet mixture attached to valve 43 and the outlet vapor mixture attached to valve 44 two separate readings of the percent of hydrocarbon vapor by volume in the respective samples will be obtained and by utilizing the graph at FIG. 5, these values for percent hydrocarbon in vapor entering the vapor recovery unit can be read across to intersect with the percent. hydrocarbon in vapor leaving the vapor recovery unit which is read up and from the point of intersection, the percent vapor recovery by volume for a given hydrocarbon vapor recovery system or unit can be easily determined.

Where it is desirable to check the performance of a hydrocarbon vapor recovery unit on the basis of the percent recovery by weight, the volume performance must be corrected for the relative molecular weights of the recovered hydrocarbons and nonrecovered hydrocarbons.

To make this weight adjustment the average molecular weight of the entering hydrocarbon and leaving hydrocarbon must be known. This information can be determined by means of chromatographic analysis of entering and leaving vapor samples.

When this information is obtained if X represents the entering average molecular weight of the hydrocarbon vapor and Y is the leaving average molecular weight of the hydrocarbon vapor, then a ratio of Y:X can be determined from these figures.

Figure 6:
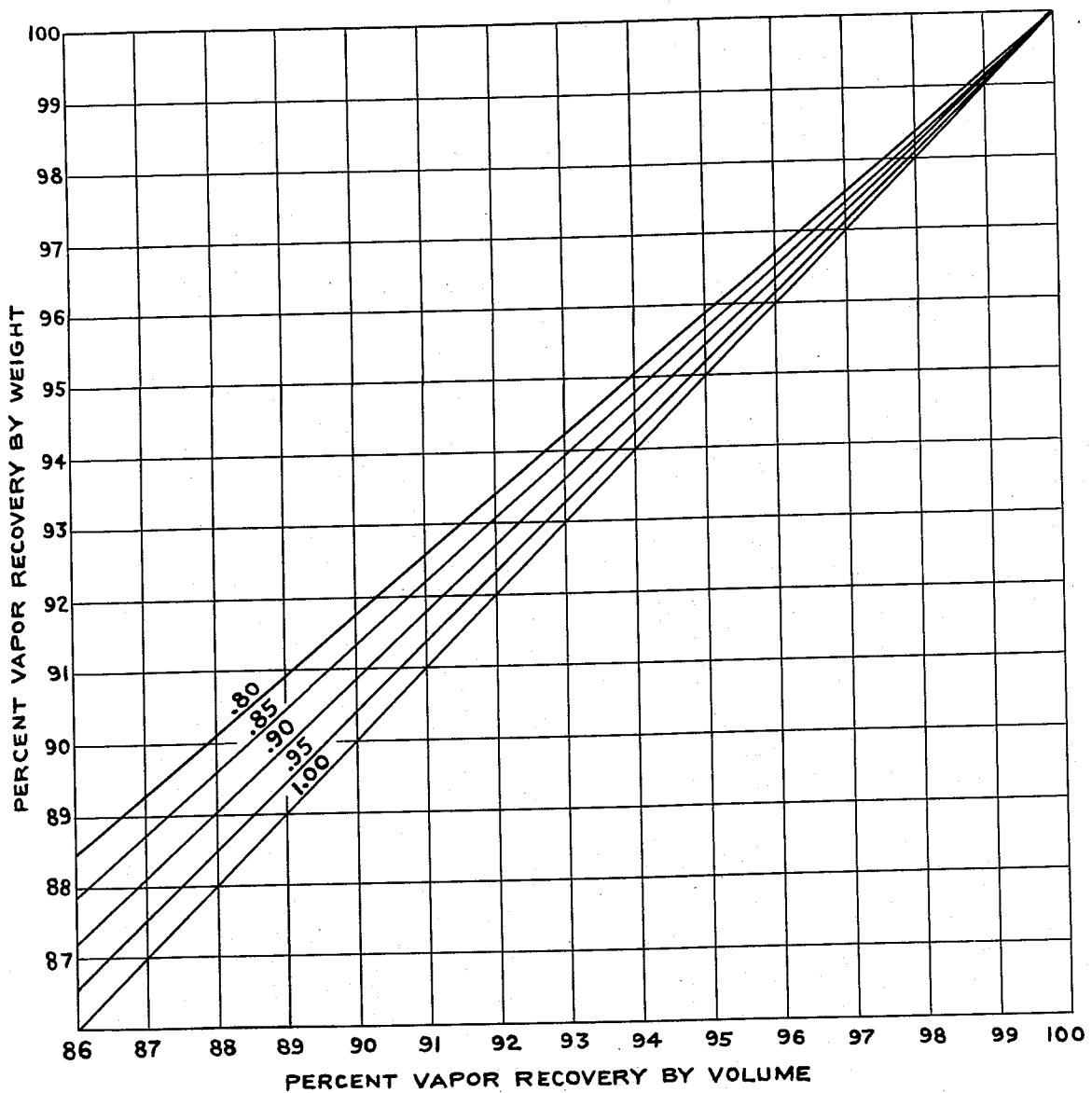
FIG. 6 is a graph by which the gravimetric efficiency of a hydrocarbon vapor recovery apparatus is determined utilizing data from application of the present invention.

FIG. 6 shows a graph in which the diagonal lines provide the representative ratio determined from the Y:X relationship and by reading up the percent vapor recovery by volume to the point where it intersects the ratio line thus determined, the percent vapor recovery by weight can be read across on the graph at FIG. 6 from the point of intersection.

VERIFICATION OF INSTRUMENT ACCURACY

Before operating the hydrocarbon vapor analyzer 10 or from time to time during the course of the use of the hydrocarbon vapor analyzer 10 it is desirable to check the accuracy thereof and this is done by charging the apparatus with a vapor mixture sample containing a non-percentage of hydrocarbon vapor and then analyzing this vapor mixture sample so that the input percentage of hydrocarbon vapor can be compared with the percentage of hydrocarbon determined by the operation of the instrument.

For this procedure the pistons 71 and 72 are first placed at the lowest most or 100 cc position and valves 43, 44, 45, 46 and 47 are closed.

The syringe 48 is filled with liquid hydrocarbon to the 5 cc level and is attached to the valve 45, then valve 45 is opened and the piston 48a of the syringe is raised to the position where the hyrocarbon liquid has just entered the connecting tube 48b for connecting the syringe 48 to the valve 45 and at this point valve 45 is closed.

Valve 43 or 44 is now opened and the graduated cylinder 13 is purged by running piston 71 up and down the burette by rotation of the crank 92 in the manner above described and the piston is returned to the lower most or 100 cc position.

At least 60 cc of air is now drawn into the graduated cylinder 13 through either valve 43 or 44 by positioning the piston 71 by means of the crank 92 at the 40 cc graduation mark then which ever valve 43 or 44 has been opened is moved to the closed position.

The valve 45 to which the syringe 48 is attached is then again opened and piston 71 is lowered by the crank 92 until the piston in the syringe engages the roller stop 48c connected to the body of the syringe 48 as is shown in FIG. 1.

Piston 71 is now raised and as it draws a vacuum on the system the syringe piston 48a will start to move upwardly into the syringe 48. The piston 71 will continue to be raised until the liquid hydrocarbon in the syringe 48 is just touching the top of the syringe but not entering the connecting tube 48b. The syringe piston 48a is now manually raised until the liquid hydrocarbon is just entering the connecting tube 48b and at this point the valve 45 is quickly closed so that no liquid hydrocarbon enters the system.

Valve 46 is now opened slowly and if piston 71 has been raised as described above, the gauge 50 will indicate a slight negative pressure. After checking this pressure the pressure gauge 50 is then brought to a zero pressure setting by adjusting the setting of the piston 71 by rotating the crank 92.

The volume of vapor in the graduated cylinder 13 is now read and this reading is substracted from the reading of the burette at the negative pressure setting and the difference is the percent of hydrocarbon in graduated cylinder 13 after performing a still further verification step.

The analyzer is further verified by closing the valve 46 and opening valve 43 or 44 and rotating the crank 92 to move the piston 71 to the upper most or zero position of the graduation.

The percent of hydrocarbon in the vapor mixture sample now in the graduated cylinder 13 can now be determined by the same steps of the previously described procedure in respect of a vapor mixture sample being analyzed by the instrument. This is accomplished by opening valve 47, balancing out the system to atmospheric pressure, closing the balancing valve either 43 or 44 as the case may be and then engaging the clutch by tightening the wing nut 106 so that the piston 71 and 72 can be moved to transfer the vapor sample from graduated cylinder 13 through the absorber 19 into the graduated cylinder 14 where the number of graduations above the piston are read to show the percentage of hydrocarbon vapor present in the vapor mixture sample that was charged into the graduated cylinder 13.

If these last mentioned procedures are carefully executed the percent of hydrocarbon vapor in the known sample should correspond within a few percentages with the results obtained utilizing the analysis procedures during normal operation of this analyzer 10.

After verifying the hydrocarbon vapor analyzer 10, the analyzer is operable for general application to only hydrocarbon vapor containing ambients by again observing the analytical procedures for analyzing a vapor mixture sample as set forth under the steps for operating the analyzer 10 above.

While the operational aspects of the hydrocarbon vapor analyzer 10 have been disclosed in terms of its preferred use for hydrocarbon vapor systems or for the bulk handling of gasoline, such as gasoline terminals or cargo vessel unloading and loading terminals, it is believed that those persons skilled in the art will recognize that the absorption of portions of gaseous mixtures so as to provide a differential volumetric measurement from the initial vapor mixture charged into the system is adaptable for other uses and for analysis of other vapors than hydrocarbon vapors.

While the foregoing description illustrates the preferred embodiment of the present invention, it will be appreciated that certain changes and modifications may be made without departing from the spirit and scope of the invention as is defined by the claims hereinafter set forth.

What is claimed is:

1. An instrument for analyzing the percent by volume of hydrocarbon vapor and the like components forming part of a vapor mixture comprising,
    a. base means including, an instrument panel,
    b. a first graduated cylinder mounted substantially vertically on said instrument panel to be utilized for receiving a sample of the vapor mixture to be analyzed,
    c. a second graduated cylinder mounted substantially vertically and in spaced relation to said first graduated cylinder to be utilized for providing a direct measurement equivalent to the percent by volume of the component being measured in the vapor mixture sample, d. valve manifold means having a central passage extending therethrough,
e. said sample receiving cylinder connected in fluid tight engagement on said valve manifold and a connecting passage in said valve manifold to connect said cylinder with the centrally disposed passage therein,
f. an inlet valve means on said valve manifold in communication with the central passage for passing a vapor mixture sample to be analyzed to said sample receiving cylinder
g. a transfer valve on said valve manifold in communication with the central passage therein,
h. an absorber for absorbing the component to be measured connected at one end to the transfer valve and at the remote end thereof to the measuring cylinder whereby on opening of the transfer valve the vapor mixture sample can be passed through the absorber and the unabsorbed portion of the vapor mixture delivered to said measuring cylinder,
i. pump means connected to said sample receiving cylinder and said measuring cylinder for filling and emptying the sample receiving cylinder with the given vapor mixture sample to be analyzed, and for transferring the vapor mixture sample from the sample receiving cylinder to the measuring cylinder, and
j. gauge means operatively associated with the sample receiving cylinder and the measuring cylinder for providing measured parameters to control the transfer of the vapor mixture sample from the sample receiving cylinder to the measuring cylinder during analysis for the component being measured.

2. In an instrument as claimed in claim 1 wherein,
a. said pump means includes, a first reciprocatable piston slidably disposed in said sample receiving cylinder, and a second reciprocatable piston slidably disposed in said measuring cylinder, and
b. actuating means for operating said pistons independently of each other and alternatively and selectively simultaneously as required during the operation of said instrument.

3. In an instrument as claimed in claim 2 wherein,
a. a first elongated rack connected to said first piston is disposed in the longitudinal line of said sample receiving piston and sized to extend a predetermined distance beyond the end of said sample receiving cylinder remote from the valve manifold end thereof;
b. a first pinion gear mounted on said instrument panel for operative engagement with said first elongated rack, and
c. a first crank means for driving the first pinion gear for independent reciprocation of said first piston,
d. a second elongated rack connected to said second piston disposed to extend in the longitudinal line of the measuring cylinder and sized to extend beyond the open end of the measuring cylinder a predermined distance,
e. a second pinion gear mounted on said instrument panel for operative engagement with said second elongated rack, and
f. a second crank means for driving the second pinion gear for independent reciprocation of said second piston.

4. In an instrument as claimed in claim 2 wherein the actuating means for simultaneously reciprocating the first piston and second piston includes,
a. first pulley means fixedly mounted and connected for movement by said first crank,
b. said pulley means freely mounted on said second crank means,
c. pulley belt means connected about said first pulley means and said second pulley means,
d. clutch means operatively connectable between said second pulley means and said second crank means, and
e. means on said second crank means for engaging said clutch means whereby on rotation of said first pulley means, said second pulley means will be simultaneously rotated by said pulley belt means.

5. In an instrument as claimed in claim 1 wherein said gauge means includes,
a. a first pressure gauge connected to said sample receiving cylinder,
b. a second pressure gauge connected to said measuring cylinder, and
c. a system pressure gauge operatively connected to said sample receiving cylinder and to said measuring cylinder.

6. In an instrument as claimed in claim 1 wherein,
a. said absorber defines a chamber for absorbing material,
b. the absorbing material in said absorber is a charge of activated charcoal for absorbing hydrocarbon vapor.

7. In an instrument as claimed in claim 1 wherein,
a. the absorber is an elongated cylindrical member defining an absorbing chamber,
b. removable cap means connected to said elongated cylindrical member at the respective opposite ends thereof to permit the absorbing chamber to be filled with absorbing material, and
c. absorbing material in said absorbing chamber for absorbing the component of the vapor mixture sample being measured.

* * * * *